(12) United States Patent
Hou et al.

(10) Patent No.: US 10,000,448 B2
(45) Date of Patent: Jun. 19, 2018

(54) CATALYSTS, METHODS, AND SYSTEMS FOR PREPARING CARBAMATES

(71) Applicant: EAST CHINA UNIVERSITY OF SCIENCE AND TECHNOLOGY, Shanghai (CN)

(72) Inventors: Zhenshan Hou, Shanghai (CN); Ran Zhang, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days. days.

(21) Appl. No.: 15/124,397

(22) PCT Filed: Mar. 13, 2014

(86) PCT No.: PCT/CN2014/073363
§ 371 (c)(1),
(2) Date: Sep. 8, 2016

(87) PCT Pub. No.: WO2015/135176
PCT Pub. Date: Sep. 17, 2015

(65) Prior Publication Data
US 2017/0015622 A1 Jan. 19, 2017

(51) Int. Cl.
*C07C 269/04* (2006.01)
*B01J 21/00* (2006.01)
(Continued)

(52) U.S. Cl.
CPC ............ *C07C 269/04* (2013.01); *B01J 21/00* (2013.01); *B01J 23/10* (2013.01); *B01J 23/14* (2013.01);
(Continued)

(58) Field of Classification Search
None
See application file for complete search history.

(56) References Cited

U.S. PATENT DOCUMENTS 4,714,694 A * 12/1987 Wan .................... B01D 53/945
502/304
2010/0191010 A1 7/2010 Bosman et al.
2013/0079546 A1 3/2013 Takamatsu et al.

FOREIGN PATENT DOCUMENTS

CN 103172538 A 6/2013
CN 103172541 A 6/2013
(Continued)

OTHER PUBLICATIONS

CAS summary for JP 2010119969 (obtained from SciFinder on Oct. 27, 2017, p. 1-4) (Year: 2017).*
(Continued)

*Primary Examiner* — Jafar Parsa
*Assistant Examiner* — Amy C Bonaparte (57) ABSTRACT

Methods, systems and kits for preparing carbamates as well as catalysts for preparing the carbamates, are disclosed. The methods for preparing carbamate can include providing a catalyst comprising cerium oxide ($CeO_2$) and at least one metal selected from the group consisting of iron (Fe), manganese (Mn), titanium (Ti), cobalt (Co), aluminum (Al), zinc (Zn), calcium (Ca), tin (Sn), indium (In), and any combination thereof; contacting the catalyst with at least one amine and at least one alcohol to form a mixture; and contacting the mixture with carbon dioxide under conditions sufficient to form the carbamate.

14 Claims, 2 Drawing Sheets

(51) Int. Cl.
    *B01J 23/10*     (2006.01)
    *B01J 23/34*     (2006.01)
    *B01J 23/83*     (2006.01)
    *B01J 23/94*     (2006.01)
    *B01J 23/92*     (2006.01)
    *B01J 23/14*     (2006.01)

(52) U.S. Cl.
    CPC ............... *B01J 23/34* (2013.01); *B01J 23/83* (2013.01); *B01J 23/92* (2013.01); *B01J 23/94* (2013.01); *B01J 2523/31* (2013.01); *B01J 2523/3712* (2013.01); *B01J 2523/60* (2013.01); *Y02P 20/584* (2015.11)

(56) References Cited

FOREIGN PATENT DOCUMENTS

| | | | |
|---|---|---|---|
| JP | 2006022043 | A | 1/2006 |
| JP | 2010119969 | * | 6/2010 |
| JP | 2012250930 | A | 12/2012 |
| KR | 101480145 | * | 1/2015 |

OTHER PUBLICATIONS

Beckers ("Selective Hydrogen Oxidation Catalysts via Genetic Algorithms" Adv. Synth. Catal. 2008, 350, 2237-2249) (Year: 2008).*

Arango-Diaz ("Comparative study of CuO supported on $CeO_2$, $Ce_{0.8}Zr_{0.2}O_2$ and $Ce_{0.8}Al_{0.2}O_2$ based catalysts in the CO-PROX reaction" International Journal of Hydrogen Energy, 39, 2014, p. 4102-4108—first publicly available on May 11, 2013). (Year: 2013).*

Tu ("Catalytic combustion of methane on $Ce_{1-x}M_xO_2$-(M=Si, Mg, Al) oxides" Indian Journal of Chemistry, vol. 53A, Feb. 2014, p. 167-173). (Year: 2014).*

Jin ("Synthesis of three-dimensionally ordered macroporous Al—Ce mixed oxide catalyst with high catalytic activity and stability for diesel soot combustion" Catalysis Today 258, 2015, p. 487-497) (Year: 2015).*

English language translation of Morisaka (JP 2010119969, Jun. 3, 2010, p. 1-42).*

Abla, M., et al., "Halogen-free process for the conversion of carbon dioxide to urethanes by homogeneous catalysis," Chemical Communications, vol. 33, Issue 21, pp. 2238-2239 (2001).

Abla, M., et al., "Nickel-catalyzed dehydrative transformation of $CO_2$ to urethanes," Green Chemistry, vol. 6, Issue 10, pp. 524-525 (2004).

Honda, M., et al., "Heterogeneous $CeO_2$ catalyst for the one-pot synthesis of organic carbamates from amines, $CO_2$ and alcohols," Green Chemistry, vol. 13, Issue 12, pp. 3406-3413 (2011).

International Search Report and Written Opinion for International Application No. PCT/US2014/073363, dated Dec. 4, 2014, 13 Pages.

Ion, A., et al., "Green synthesis of carbamates from $CO_2$, amines and alcohols," Green Chemistry, vol. 10, Issue 1, pp. 111-116 (2008).

* cited by examiner

CATALYSTS, METHODS, AND SYSTEMS FOR PREPARING CARBAMATES

CROSS-REFERENCE TO RELATED APPLICATION

This Patent Application is a U.S. National Stage filing under 35 U.S.C. § 371 of International Application No. PCT/CN2014/073363, filed on Mar. 13, 2014, entitled "CATALYSTS, METHODS, AND SYSTEMS FOR PREPARING CARBAMATES," the entire content of which is incorporated herein by reference in its entirety for any and all purposes.

BACKGROUND

Unless otherwise indicated herein, the materials described in this section are not prior art to the claims in this application and are not admitted to be prior art by inclusion in this section.

Carbamates have important applications in industry. Conventional synthesis methods generally involve preparing carbamates by alcoholysis and aminolysis using phosgene as a raw material. Many countries have taken initiatives to find novel synthesis processes to gradually replace the methods that use phosgene. In addition, in recent years, environmental issues have resulted in increasing attention. In particular, the rise in carbon dioxide levels in the global environment has led to an increased desire to fix and comprehensively use carbon dioxide as a potential carbon resource, while ensuring energy conservation and emission reduction. As carbon dioxide is stable, non-toxic, non-corrosive, flame-retardant and easily processed, it is one of the most widely distributed, most abundant in storage and cheapest carbon resource.

Accordingly, a desire has been to use carbon dioxide to replace limited and non-renewable petrochemical resources by C1 synthetic reaction and to prepare useful compounds by various chemical conversions. Such use has both important application values and theoretical research significance. Methods for synthesizing organic carbamates in one step using carbon dioxide, organic amine and alcohol as raw materials have drawn interest. However, the activity of catalysts used in synthesizing organic carbamates is often poor for aliphatic amines. Aliphatic amines are cheaper to use and less toxic than aromatic amines. Consequently, there is a need for methods of preparing carbamates using carbon dioxide as a raw material and using a reusable, highly active, efficient and more inexpensive catalyst.

SUMMARY

Some embodiments disclosed herein describe a catalyst comprising cerium oxide ($CeO_2$) and at least one metal selected from the group consisting of iron (Fe), manganese (Mn), titanium (Ti), cobalt (Co), aluminum (Al), zinc (Zn), calcium (Ca), tin (Sn), indium (In), and any combination thereof. In some embodiments, the catalyst can be a heterogeneous catalyst.

Some embodiments disclosed herein describe methods for preparing a catalyst. The method can include providing a first solution comprising at least one metal nitrate selected from the group consisting of iron (Fe) nitrate, manganese (Mn) nitrate, titanium (Ti) nitrate, cobalt (Co) nitrate, aluminum (Al) nitrate, zinc (Zn) nitrate, calcium (Ca) nitrate, tin (Sn) nitrate, indium (In) nitrate, and any combination thereof; contacting the first solution with a material comprising cerium to form a second solution; and contacting a base with the second solution to form a suspension of the catalyst.

Some embodiments disclosed herein describe methods of preparing carbamate. The method can include providing a catalyst comprising cerium oxide ($CeO_2$) and at least one metal selected from the group consisting of iron (Fe), manganese (Mn), titanium (Ti), cobalt (Co), aluminum (Al), zinc (Zn), calcium (Ca), tin (Sn), indium (In), and any combination thereof; contacting the catalyst with at least one amine and at least one alcohol to form a mixture; and contacting the mixture with carbon dioxide under conditions sufficient to form the carbamate. In some embodiments, the catalyst can be a heterogeneous catalyst.

Some embodiments disclosed herein describe a system for preparing carbamate. The system can include an enclosure configured to receive a catalyst, at least one amine, at least one alcohol, and carbon dioxide; and a mixer configured to contact the catalyst, the at least one amine, and the at least one alcohol, with the carbon dioxide, wherein the catalyst comprises cerium oxide ($CeO_2$) and at least one metal selected from the group consisting of iron (Fe), manganese (Mn), titanium (Ti), cobalt (Co), aluminum (Al), zinc (Zn), calcium (Ca), tin (Sn), indium (In), and any combination thereof.

Some embodiments disclosed herein describe a kit for preparing carbamate. The kit can include a catalyst; at least one amine; at least one alcohol; and instructions for contacting the catalyst, the at least one amine, and the at least one alcohol with carbon dioxide to prepare the carbamate, wherein the catalyst comprises cerium oxide ($CeO_2$) and at least one metal selected from the group consisting of iron (Fe), manganese (Mn), titanium (Ti), cobalt (Co), aluminum (Al), zinc (Zn), calcium (Ca), tin (Sn), indium (In), and any combination thereof. In some embodiments, the kit may further include carbon dioxide.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Carbamates have important industrial applications by using carbon dioxide, organic amines and methanol as raw materials under mild reaction conditions. Carbamates can be used as organic solvents as well as organic intermediates to manufacture plastics, rubbers, fiber, rigid and soft foamed plastics, adhesives and coatings.

Disclosed herein are catalysts, methods, systems and kits for preparing carbamates as well as methods for preparing catalysts for use in the same. The carbamates prepared by the methods, systems or kits disclosed herein can be cyclic or non-cyclic.

Catalysts

Catalysts that can be used to prepare materials, such as carbamates, using carbon dioxide are disclosed herein. In some embodiments, a catalyst can include cerium oxide ($CeO_2$) and at least one metal. Non-limiting examples of the metal include iron (Fe), manganese (Mn), titanium (Ti), cobalt (Co), aluminum (Al), zinc (Zn), calcium (Ca), tin (Sn), indium (In), and any combination thereof. In some embodiments, the metal comprises iron (Fe), manganese (Mn), titanium (Ti), cobalt (Co), aluminum (Al), zinc (Zn), calcium (Ca), tin (Sn), indium (In), or any combination thereof. In some embodiments, the catalyst is a heterogeneous catalyst.

In some embodiments, for example, the metal is aluminum. In some embodiments, the catalyst includes cerium oxide ($CeO_2$) and aluminum (Al). The amount of $CeO_2$ and Al in the catalyst can vary. For example, the catalyst can have a formula $Ce_xAl_yO_2$, wherein x and y add up to about 1, and x and y are each a positive number. In some embodiments, x can be about 0.8 to about 1, and y can be about 0 to about 0.2. For example, in some embodiments, x can be about 0.8, about 0.81, about 0.82, about 0.83, about 0.84, about 0.85, about 0.86, about 0.87, about 0.88, about 0.89, about 0.90, about 0.91, about 0.92, about 0.93, about 0.94, about 0.95, about 0.96, about 0.97, about 0.98, about 0.99, about 1, or a range between any two of these values; and y can be about 0.2, about 0.19, about 0.18, about 0.17, about 0.16, about 0.15, about 0.14, about 0.13, about 0.12, about 0.11, about 0.10, about 0.09, about 0.08, about 0.07, about 0.06, about 0.05, about 0.04, about 0.03, about 0.02, about 0.01, about 0, or a range between any two of these values. In some embodiments, x is about 0.9 to about 1, and y is about 0 to about 0.1. In some embodiments, x is about 0.95 to about 1, and y is about 0 to about 0.05. In some embodiments, x is about 0.96 to about 1, and y is about 0 to about 0.04. In some embodiments, x is about 0.97 to about 1, and y is about 0 to about 0.03. In some embodiments, x is about 0.96 to about 0.97, and y is about 0.03 to about 0.04. In some embodiments, x is about 0.966 and y is about 0.033. In some embodiments, x can be 0.966 and y can be 0.033.

Methods for Preparing Catalysts

The present disclosure, in some embodiments, describes methods related to preparing catalysts for synthesizing materials, such as carbamates. The methods described herein can be non-toxic and environmentally friendly. The raw materials for preparing the catalysts can be inexpensive and readily available. The methods disclosed herein can be simple and easy to operate. The catalyst can also be reusable. The catalyst can be suitable for a wide range of substrates. In addition, the catalyst can efficiently catalyze the reaction between aliphatic amines or benzylamine and carbon dioxide and alcohol to produce carbamate.

The method of preparing the catalyst, in some embodiments, includes providing a first solution that includes at least one metal nitrate; contacting the first solution with a material that includes cerium to form a second solution; and contacting a base with the second solution to form a suspension of the catalyst. Non-limiting examples of the metal nitrate include iron (Fe) nitrate, manganese (Mn) nitrate, titanium (Ti) nitrate, cobalt (Co) nitrate, aluminum (Al) nitrate, zinc (Zn) nitrate, calcium (Ca) nitrate, tin (Sn) nitrate, indium (In) nitrate, and any combination thereof.

Figure 1:
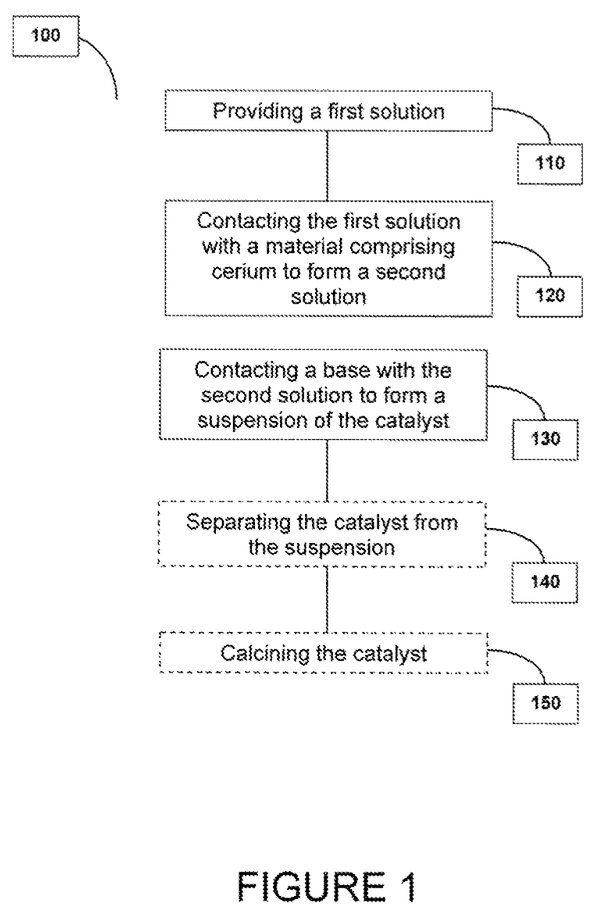
FIG. 1 is a flow diagram illustrating a non-limiting example of a method of preparing a catalyst.

A non-limiting example of the method 100 of preparing the catalyst in accordance with the present disclosure is illustrated in the flow diagram shown in FIG. 1. As illustrated in FIG. 1, method 100 can include one or more functions, operations or actions as illustrated by one or more operations 110-150.

Method 100 can begin at operation 110, "Providing a first solution." Operation 110 can be followed by operation 120, "Contacting the first solution with a material comprising cerium to form a second solution." Operation 120 can be followed by operation 130, "Contacting a base with the second solution to form a suspension of the catalyst." Operation 130 can be followed by optional operation 140, "Separating the catalyst from the suspension." Operation 140 can be followed by optional operation 150, "Calcining the catalyst."

In FIG. 1, operations 110-150 are illustrated as being performed sequentially with operation 110 first and operation 150 last. It will be appreciated, however, that these operations can be combined and/or divided into additional or different operations as appropriate to suit particular embodiments. For example, additional operations can be added before, during or after one or more operations 110-150. In some embodiments, one or more of the operations can be performed at about the same time.

At operation 110, "Providing a first solution," the first solution can include at least one metal nitrate. The metal nitrate can be iron (Fe) nitrate, manganese (Mn) nitrate, titanium (Ti) nitrate, cobalt (Co) nitrate, aluminum (Al) nitrate, zinc (Zn) nitrate, calcium (Ca) nitrate, tin (Sn) nitrate, indium (In) nitrate, or any combination thereof. In some embodiments, the first solution includes titanium (Ti) nitrate, cobalt (Co) nitrate, aluminum (Al) nitrate, (Fe) nitrate, manganese (Mn) nitrate, or any combination thereof. The content of the metal in the first solution can vary. For example, the metal can be presented in the first solution at a concentration of about 0.5 mg/mL to about 5 mg/mL. In some embodiments, the metal is presented in the first solution at a concentration of about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, or a range between any two of these values.

At operation 120, "Contacting the first solution with a material comprising cerium to form a second solution," in some embodiments, the material comprising cerium can include cerium nitrate. In some embodiments, the cerium nitrate can be hydrated cerium nitrate. In some embodiments, the hydrated cerium nitrated can be cerium nitrate hexahydrate ($Ce(NO_3)_3 \cdot 6H_2O$). In some embodiments, the cerium nitrate is ceric ammonium nitrate ($(NH_4)_2Ce(NO_3)_6$). In some embodiments, the material comprising cerium is hydrated cerium. In some embodiments, the hydrated cerium is ammonium cerium (IV) sulfate hydrate, cerium (III) acetate hydrate and any combination thereof.

In some embodiments, the metal comprising cerium is cerium nitrate. The molar ratio of cerium nitrate to metal nitrate in the second solution is not particularly limited. For example, the molar ratio of cerium nitrate to metal nitrate in the second solution can be about 5:1 to about 50:1. In some embodiments, the molar ratio of cerium nitrate to metal nitrate in the second solution can be about 5:1, about 6:1, about 7:1, about 8:1, about 9:1, about 10:1, about 12:1, about 14:1, about 16:1, about 18:1, about 20:1, about 22:1, about 24:1, about 26:1, about 28:1, about 30:1, about 32:1, about 34:1, about 36:1, about 38:1, about 40:1, about 42:1, about 44:1, about 46:1, about 48:1, about 50:1, or a range between any two of these values. In some embodiments, the molar ratio of cerium nitrate to metal nitrate in the second solution can be about 28:1 to about 30:1. In some embodiments, the molar ratio of cerium nitrate to metal nitrate in the second solution is about 28:1. In some embodiments, the molar ratio of cerium nitrate to metal nitrate in the second solution is about 29:1. In some embodiments, the molar ratio of cerium nitrate to metal nitrate in the second solution is about 30:1.

At operation 130, "Contacting a base with the second solution to form a suspension of the catalyst," the base to be contacted can vary. Examples of the base include, but are not limited to, ammonia ($NH_3$), ammonia complexed with water ($NH_3.H_2O$), sodium hydroxide (NaOH), potassium hydroxide (KOH), sodium carbonate ($Na_2CO_3$), potassium carbonate ($K_2CO_3$), and any combinations thereof. In some embodiments, the base can include ammonia. In some embodiments, the ammonia can include $NH_3.H_2O$. In some embodiments, the base can include sodium hydroxide (NaOH), potassium hydroxide (KOH), sodium carbonate ($Na_2CO_3$), potassium carbonate ($K_2CO_3$), or any combination thereof. The pH of the second solution is not particularly limited. For example, in some embodiments, contacting the base with the second solution can include adding the base until the second solution has a pH of about 6 to about 11. For example, in some embodiments, the pH of the second solution can be about 6, about 7, about 8, about 9, about 10, about 11, or a range between any two of these values. In some embodiments, contacting the base with the second solution can include adding the base until the second solution has a pH of about 8 to about 10.

At operation 130, "Contacting a base with the second solution to form a suspension of the catalyst," contacting a base with the second solution to form a suspension of the catalyst can include mixing the base and the second solution. The amount of time for which the base and the second solution is mixed is not particularly limited. In some embodiments, the base and the second solution can be mixed for about two to about ten hours. For example, the base and the second solution can be mixed for about two hours, about three hours, about four hours, about five hours, about six hours, about seven hours, about eight hours, about nine hours, about ten hours or a range between any two of these values. In some embodiments, the base and the second solution can be mixed for about three hours.

At optional operation 140, "Separating the catalyst from the suspension," the method by which the catalyst is separated from the suspension is not particularly limited. For example, the catalyst can be separated from the suspension by centrifugation, filtration or both.

At optional operation 150, "Calcining the catalyst," the amount of time for which the catalyst is calcined is not particularly limited. In some embodiments, the catalyst can be calcined for about two to about ten hours. For example, the catalyst can be calcined for about two hours, about three hours, about four hours, about five hours, about six hours, about seven hours, about eight hours, about nine hours, about ten hours or a range between any two of these values. In some embodiments, the catalyst can be calcined for about three hours. The temperature at which the catalyst is calcined can also vary. For example, in some embodiments, the catalyst can be calcined at an elevated temperature, such as a temperature of about 300° C. to about 800° C. In some embodiments, the catalyst can be calcined at about 300° C., about 350° C., about 400° C., about 450° C., about 500° C., about 550° C., about 600° C., about 650° C., about 700° C., about 750° C., about 800° C., or a range between any two of these values. For example, in some embodiments, the catalyst can be calcined at about 500° C. to about 600° C. The location or device in which the catalyst can be calcined is not particularly limited. For example, in some embodiments, the catalyst can be calcined in a tube furnace, a Muffle furnace or both.

Methods of Preparing Carbamates

The present disclosure, in some embodiments, describes methods related to preparing carbamates, for example, cyclic or non-cyclic carbamates. The method, in some embodiments, includes providing a catalyst comprising cerium oxide ($CeO_2$) and at least one metal; contacting the catalyst with at least one amine and at least one alcohol to form a mixture; and contacting the mixture with carbon dioxide under conditions sufficient to form the carbamate. Non-limiting examples of the metal include iron (Fe), manganese (Mn), titanium (Ti), cobalt (Co), aluminum (Al), zinc (Zn), calcium (Ca), tin (Sn), indium (In), and any combination thereof. In some embodiments, the method of preparing carbamate can further include an internal standard. Non-limiting examples of the internal standard include toluene, octane, isooctane, dodecane, and any combinations thereof. In some embodiments, for example, the internal standard can include toluene. In other embodiments, the internal standard can include octane, isooctane, dodecane, or a combination thereof.

Figure 2:
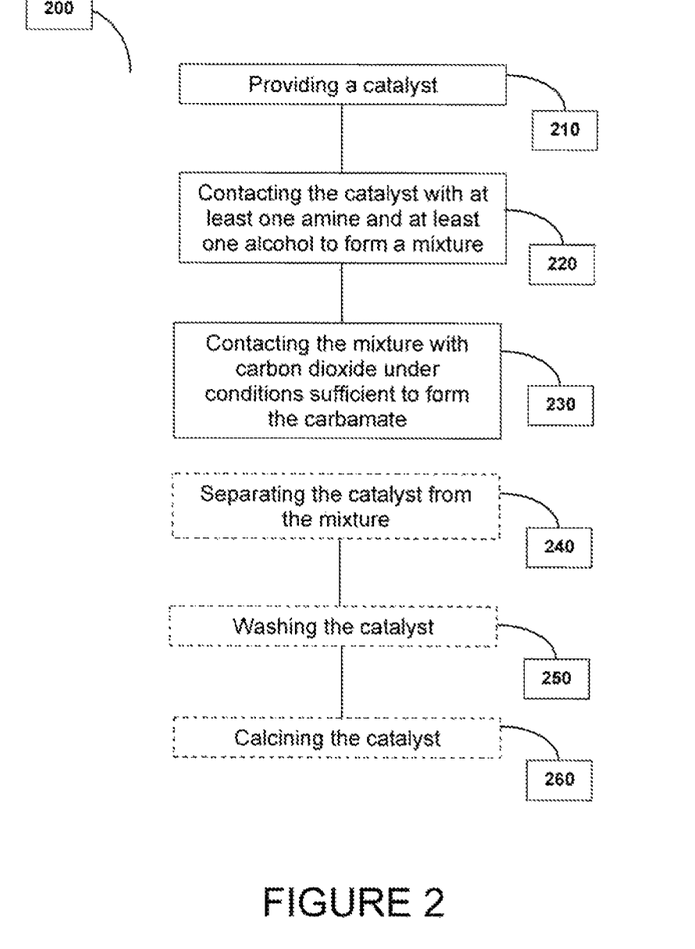
FIG. 2 is a flow diagram illustrating a non-limiting example of a method of preparing carbamate.

A non-limiting example of the method 200 of preparing carbamates in accordance with the present disclosure is illustrated in the flow diagram shown in FIG. 2. As illustrated in FIG. 2, method 200 can include one or more functions, operations or actions as illustrated by one or more operations 210-260.

Method 200 can begin at operation 210, "Providing a catalyst." Operation 210 can be followed by operation 220, "Contacting the catalyst with at least one amine and at least one alcohol to form a mixture." Operation 220 can be followed by operation 230, "Contacting the mixture with carbon dioxide under conditions sufficient to form the carbamate." Operation 230 can optionally be followed by operation 240, "Separating the catalyst from the mixture." Operation 240 can optionally be followed by operation 250, "Washing the catalyst." Operation 260 can optionally be followed by operation 260, "Calcining the catalyst."

In FIG. 2, operations 210-260 are illustrated as being performed sequentially with operation 210 first and operation 260 last. It will be appreciated, however, that these operations can be combined and/or divided into additional or different operations as appropriate to suit particular embodiments. For example, additional operations can be added before, during or after one or more operations 210-260. In some embodiments, one or more of the operations can be performed at about the same time.

At operation 210, "Providing a catalyst," the catalyst can include cerium oxide ($CeO_2$) and at least one metal. The metal can be iron (Fe), manganese (Mn), titanium (Ti), cobalt (Co), aluminum (Al), zinc (Zn), calcium (Ca), tin (Sn), indium (In), or any combination thereof. In some embodiments, the catalyst is a heterogeneous catalyst. A heterogeneous catalyst is defined here as a catalyst in which the phase, for example, solid, liquid, gas, varies from the phase of the reactants.

At operation 220, "Contacting the catalyst with at least one amine and at least one alcohol to form a mixture," in some embodiments, the at least one alcohol can include methanol, ethanol, propanol, butanol, n-hexanol, or a combination thereof. In some embodiments, the at least one amine can include at least one aliphatic amine. For example, in some embodiments, the at least one aliphatic amine can include methylamine, ethylamine, n-propylamine, n-butylamine, n-hexylamine, n-octylamine or a combination thereof. In some embodiments, the at least one amine can include at least one aromatic amine. For example, in some embodiments, the at least one aromatic amine can include benzylamine.

The molar ratio of the at least one amine to the at least one alcohol in the mixture of operation 220 is not particular limited. For example, in some embodiments, the molar ratio can be about 1:40 to about 1:200. In some embodiments, the molar ratio can be about 1:40, about 1:50, about 1:60, about 1:70, about 1:80, about 1:90, about 1:100, about 1:110, about 1:120, about 1:130, about 1:140, about 1:150, about 1:160, about 1:170, about 1:180, about 1:190, about 1:200, or a range between any two of these values. In some embodiments, the molar ratio of the at least one amine to the at least one alcohol in the mixture is about 1:100.

At operation 230, "Contacting the mixture with carbon dioxide under conditions sufficient to form the carbamate," in some embodiments, contacting the mixture with the carbon dioxide can be performed in a high pressure reactor. In some embodiments, contacting the mixture with carbon dioxide comprises heating the mixture and the carbon dioxide at a temperature of about 160° C. to about 180° C. In some embodiments, the temperature can be about 160° C., about 162° C., about 164° C., about 166° C., about 168° C., about 170° C., about 172° C., about 174° C., about 176° C., about 178° C., about 180° C., or a range between any two of these values. In some embodiments, contacting the mixture with carbon dioxide can include heating the mixture and the carbon dioxide at a temperature of about 170° C. In some embodiments, contacting the mixture with carbon dioxide can include heating the mixture and the carbon dioxide at a pressure of about 4.0 MPa to about 7.0 MPa. In some embodiments, for example, the pressure can be about 4.0 MPa, about 4.2 MPa, about 4.4 MPa, about 4.6 MPa, about 4.8 MPa, about 5.0 MPa, about 5.2 MPa, about 5.4 MPa, about 5.6 MPa, about 5.8 MPa, about 6.0 MPa, about 6.2 MPa, about 6.4 MPa, about 6.6 MPa, about 6.8 MPa, about 7.0 MPa, or a range between any two of these values. In some embodiments, contacting the mixture with carbon dioxide can include heating the mixture and the carbon dioxide at a pressure of about 5.0 MPa.

In some embodiments, contacting the mixture with carbon dioxide can include heating the mixture and the carbon dioxide. The time period for which the mixture is heated can vary. In some embodiments, contacting the mixture with carbon dioxide comprises heating the mixture and the carbon dioxide for about 2 hours to about 16 hours. In some embodiments, heating the mixture and the carbon dioxide can occur for about 2 hours, about 4 hours, about 6 hours, about 8 hours, about 10 hours, about 12 hours, about 14 hours, about 16 hours, or a range between any two of these values. In some embodiments, heating the mixture and the carbon dioxide can occur for about 8 hours to about 12 hours. In some embodiments, heating the mixture and the carbon dioxide can occur for about 8 hours, about 9 hours, about 10 hours, about 11 hours, or about 12 hours.

In some embodiments, the amount of the amine converted as a molar percentage of an initial amount of the amine before the contacting step 220 (herein referred to as "percentage of the amine converted"), can be at least about 36%. In some embodiments, the percentage of the amine converted to the carbamate can be about 36% to about 94%. For example, in some embodiments, the percentage of the amine converted to the carbamate can be about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 91%, about 92%, about 93%, about 94%, or a range between any two of these values.

In some embodiments, the selectivity of the carbamate can be at least about 34%. In some embodiments, the selectivity of the carbamate can be about 34% to about 93%. For example, in some embodiments, the selectivity of the carbamate can be about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 91%, about 92%, about 93%, or a range between any two of these values. As used herein, the selectivity of the carbamate is defined as a molar percentage of the carbamate in the products of the contacting step. The molar percentage of carbamate is determined by dividing moles of carbamate by total moles of products converted from the amine.

At optional operation 240, "Separating the catalyst from the mixture," the method of preparing carbamate can further include separating the catalyst from the mixture. In some embodiments, the separating step includes centrifugation, filtration or both.

At optional operation 250, "Washing the catalyst," the method of preparing carbamate can further include washing the catalyst. In some embodiments, washing the catalyst can include washing the catalyst with at least one alcohol. The type of the at least one alcohol can vary. In some embodiments, for example, the at least one alcohol can include methanol, ethanol, propanol, butanol, n-hexanol, or a combination thereof.

At optional operation 260, "Calcining the catalyst," the method of preparing carbamate can further include calcining the catalyst. The amount of time for which the catalyst is calcined is not particularly limited. In some embodiments, the catalyst can be calcined for about two to about ten hours. For example, the catalyst can be calcined for about two hours, about three hours, about four hours, about five hours, about six hours, about seven hours, about eight hours, about nine hours, about ten hours or a range between any two of these values. In some embodiments, the catalyst can be calcined for about three hours. In some embodiments, the catalyst is calcinated for about 4 hours.

The temperature at which the catalyst is calcined can also vary. For example, in some embodiments, the catalyst can be calcined at a temperature of about 200° C. to about 800° C. In some embodiments, the catalyst can be calcined at a temperature of about 200° C., about 250° C., 300° C., about 350° C., about 400° C., about 450° C., about 500° C., about 550° C., about 600° C., about 650° C., about 700° C., about 750° C., about 800° C., or a range between any two of these values. In some embodiments, the catalyst is calcined at a temperature of about 200° C. The location in which the catalyst can be calcined is not particularly limited. For example, in some embodiments, the catalyst can be calcined in a tube furnace, a Muffle furnace or both.

In some embodiments, the catalyst can be reusable after separation from the mixture. In some embodiments, the catalyst can be reusable with substantially the same activity and selectivity. In some embodiments, the catalyst can be reusable for multiple times. For example, the catalyst can be used, in some embodiments, for up to twice, up to three times, up to four times, up to five times, up to six times, up to seven times, up to eight times, up to nine times, or up to ten times. In some embodiments, the catalyst can be used, in some embodiments, for at least twice, at least three times, at least four times, at least five times, at least six times, at least seven times, at least eight times, at least nine times, at least ten times, or more. In some embodiments, the catalyst is reusable for multiple times with substantially the same activity and/or selectivity. In some embodiments, the catalyst is reusable for multiple times with at least about 99%, about 95%, about 90%, about 85%, about 80% of the original activity and/or selectivity. For example, the catalyst may be reusable up to three times with substantially the same activity and selectivity.

Also disclosed herein are carbamates prepared by the methods disclosed herein. The carbamates can be non-cyclic, cyclic, or a combination thereof.

System and Kits for Preparing Carbamate

Systems and kits for preparing carbamate are also disclosed. In some embodiments, the system includes an enclosure configured to receive a catalyst, at least one amine, at least one alcohol, and carbon dioxide; and a mixer configured to contact the catalyst, the at least one amine, and the at least one alcohol, with the carbon dioxide, wherein the catalyst can include cerium oxide ($CeO_2$) and at least one metal. Non-limiting examples of the metal include iron (Fe), manganese (Mn), titanium (Ti), cobalt (Co), aluminum (Al), zinc (Zn), calcium (Ca), tin (Sn), indium (In), and any combination thereof. As disclosed herein, in some embodiments, the at least one alcohol can include methanol, ethanol, propanol, butanol, n-hexanol or a combination thereof. The amine can be an aliphatic amine, an aromatic amine, or any combination thereof. In some embodiments, the at least one amine comprises an aliphatic amine. In some embodiments, the at least one amine can include at least one aromatic amine. For example, in some embodiments, the at least one aromatic amine includes benzylamine.

The kits for preparing carbamate, in some embodiments, can include a catalyst; at least one amine; at least one alcohol; and instructions for contacting the catalyst, the at least one amine, and the at least one alcohol with carbon dioxide to prepare the carbamate, wherein the catalyst comprises cerium oxide ($CeO_2$) and at least one metal. In some embodiments, the kit may further include carbon dioxide. The carbon dioxide can for example be in a compressed liquid form, in dry ice form or other modes of storage. The at least one metal can include iron (Fe), manganese (Mn), titanium (Ti), cobalt (Co), aluminum (Al), zinc (Zn), calcium (Ca), tin (Sn), indium (In), or any combination thereof. As disclosed herein, the at least one alcohol can include methanol, ethanol, propanol, butanol, n-hexanol, or a combination thereof. In some embodiments, the at least one amine comprises at least one aliphatic amine. In some embodiments, the at least one amine comprises at least one aromatic amine.

EXAMPLES

Additional embodiments are disclosed in further detail in the following examples, which are not in any way intended to limit the scope of the claims.

Example 1

Preparation of the Catalyst

Transition metal (M) nitrate (M=Fe, Mn, Ti, Co, Al, Zn, Ca, Sn or In) was weighed and dissolved in pure water. The content of the metal in the solution was 1.0 mg/mL. Then, the pre-weighed $Ce(NO_3)_3 \cdot 6H_2O$ solid was poured into the above-formulated nitrate solution. The amount of cerous nitrate was adjusted to allow a molar ratio ($n_{Ce}/n_M$) to be 29:1. The mixture was sonicated to obtain a homogeneous solution. A solution of $NH_3 \cdot H_2O$ (1:10) was added dropwise to the reaction system under vigorous stirring to adjust the pH value of the solution to 9. It was continuously stirred for another three hours after the addition of ammonia, and a large amount of solid was separated out. The solid was suction filtered, washed with water to neutrality and dried in a vacuum drying oven overnight at 60° C. The as-prepared solid catalyst was weighed and calcined in a Muffle furnace for three hours at 600° C.

Without being bound by any particular theory, it is believed that carbamate was prepared according to the chemical reaction shown in Scheme I. In Scheme I, R is $C_nH_{2n+1}$ (n is a positive integer).

Scheme I

Example 2

Preparation of Carbamate

Carbonylation reactions were performed in a 50 mL high-pressure reactor connected with a stainless steel piezometer and thermocouple. 0.3 g of solid catalyst, as prepared according to the general procedure described in Example 1, was poured into a polytetrafluoroethylene-lined reactor. N-butylamine (5 mmol, 0.5 mL) and methanol (500 mmol, 20.3 mL) were weighed and added to the reactor with 46 µL of toluene as an internal standard. Carbon dioxide gas was fed into the reactor and then released slowly from the reactor to displace the air in the reactor. The operation was repeated three times, followed by injecting 2.5 g of carbon dioxide gas using a high-pressure pump into the reactor. The pressure at which the reaction was carried out was 5 MPa. The reactor was heated, and the stirring rate and heating rate were adjusted to a stirring rate of 1000 r/min and a heating rate of 8° C./min. After the reaction had proceeded for a period of time at a certain temperature, the reactor was cooled in an ice-water bath, and unreacted $CO_2$ was released. A small amount of product or substrate was absorbed by methanol solution. The "product" at this stage refers to carbamate and alkyl urea formed during the reaction. The "substrate" refers to the unreacted n-butylamine.

TABLES 1 and 2 show the results of the catalytic reactions. TABLE 1 shows that Ce—Al catalysts with various Ce and Al contents can be used to catalyze the reaction to form carbamate product under various conditions. For example, TABLE 1 shows the effect of reaction temperature, reaction pressure, reaction time, the molar ratio of n-butylamine and methanol, the molar ratio of Ce and Al, and calcination temperature on the catalytic activity of the catalysts containing Al. TABLE 2 shows that in addition to Al, other metals in conjunction with Ce can also form catalysts to catalyze reactions to produce carbamate product. For example, TABLE 2 shows the effect of a second metal (Co, Ti, Fe and Mn) on the catalytic activity. The Ce—Al catalyst in which the molar ratio of $n_{Ce}$ to $n_{Al}$ was 29:1, afforded the highest catalytic activity among the catalysts tested.

This example demonstrates that the catalysts disclosed herein can efficiently catalyze reactions to produce carbamate product under various conditions.

catalyst by simple centrifugation. The clear and transparent liquid in the upper layer was the reacted sample to be analyzed by gas chromatography. The selectivity of the carbamate was about 90%.

The catalyst was washed with methanol three times to remove the carbamate and alkyl urea organic products adhered to the surface and the unreacted n-butylamine substrate. The washed catalyst was transferred into a tube furnace and calcined at 200° C. for four hours to achieve dehydration and oxidative regeneration of the catalyst. The catalyst that had been dehydrated and regenerated could be directly reused, where the operation process of the experiment and the feed ratio of the substrates were approximately consistent with the first operation. The catalyst was reused three times without substantial decrease in activity and selectivity.

Accordingly, these examples demonstrate that the methods disclosed herein can be used to prepare catalysts for synthesizing materials, such as carbamates, with improved activity and selectivity. In particular, the catalysts can efficiently catalyze the reaction between aliphatic amines or benzylamine and carbon dioxide and alcohol to produce

TABLE 1

Activity and Selectivity of Different Catalysts

| Reaction Temperature/ ° C. | Reaction Pressure/ MPa | Reaction Time/h | Ratio of substrates $n_{BA}/n_{MeOH}$ | Catalyst $n_{Ce}/n_{Al}$ | Calcination Temperature/ ° C. | Conversion of n-butylamine/% | Selectivity of the carbamate/% |
|---|---|---|---|---|---|---|---|
| 170 | 5.0 | 16 | 1:40 | 43:1 | 600 | 80.5 | 78.2 |
| 170 | 5.0 | 16 | 1:40 | 29:1 | 600 | 91.0 | 81.5 |
| 170 | 5.0 | 16 | 1:40 | 9:1 | 600 | 58.3 | 46.7 |
| 170 | 5.0 | 16 | 1:40 | 4:1 | 600 | 36.5 | 34.0 |
| 170 | 5.0 | 16 | 1:40 | 29:1 | 500 | 84.8 | 74.1 |
| 170 | 5.0 | 16 | 1:40 | 29:1 | 700 | 51.0 | 63.3 |
| 150 | 5.0 | 16 | 1:40 | 29:1 | 600 | 44.7 | 80.5 |
| 170 | 6.0 | 16 | 1:40 | 29:1 | 600 | 85.3 | 85.2 |
| 170 | 5.0 | 16 | 1:100 | 29:1 | 600 | 90.6 | 92.6 |
| 170 | 5.0 | 14 | 1:40 | 29:1 | 600 | 86.0 | 78.9 |
| 170 | 5.0 | 12 | 1:40 | 29:1 | 600 | 82.4 | 84.2 |
| 170 | 5.0 | 8 | 1:40 | 29:1 | 600 | 72.4 | 83.0 |
| 170 | 5.0 | 6 | 1:40 | 29:1 | 600 | 66.8 | 82.0 |
| 170 | 5.0 | 4 | 1:40 | 29:1 | 600 | 61.4 | 81.8 |
| 170 | 5.0 | 2 | 1:40 | 29:1 | 600 | 54.5 | 77.3 |

Reaction condition:
BA = n-butylamine, MeOH = methanol, the product refers to butyl carbamate, catalyst 0.3 g.

TABLE 2

Activity and Selectivity of Different Catalysts

| Catalyst | Calcination Temperature/ ° C. | Reaction Temperature/ ° C. | Reaction Pressure/ MPa | Reaction Time/h | Ratio of substrates $n_{BA}/n_{MeOH}$ | Conversion of n-butylamine/% | Selectivity of the carbamate/% |
|---|---|---|---|---|---|---|---|
| Ce—Co | 600 | 170 | 5.0 | 16 | 1:40 | 82.1 | 76.1 |
| Ce—Ti | 600 | 170 | 5.0 | 16 | 1:40 | 67.6 | 75.9 |
| Ce—Al | 600 | 170 | 5.0 | 16 | 1:40 | 91.0 | 81.5 |
| Ce—Fe | 600 | 170 | 5.0 | 16 | 1:40 | 93.7 | 70.0 |
| Ce—Mn | 600 | 170 | 5.0 | 16 | 1:40 | 91.4 | 79.5 |

Reaction condition:
BA = n-butylamine, MeOH = methanol, the product refers to butyl carbamate, $n_{Ce}/n_{Al}$ = 29:1, catalyst 0.3 g.

Example 3

Separation of Product and Cyclic Use of Catalyst

The reaction solution (that is, the reaction mixture after the reaction performed according to the general procedure described in Example 2) was separated from the solid carbamate. As shown above, the raw materials for preparing the catalysts using the methods described herein can be inexpensive and readily available. The catalyst can also be reusable.

With respect to the use of substantially any plural and/or singular terms herein, those having skill in the art can translate from the plural to the singular and/or from the singular to volume of wastewater can be received in the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

What is claimed is:

1. A catalyst comprising cerium oxide ($CeO_2$) and aluminum (Al) comprising formula $Ce_xAl_yO_2$, wherein the catalyst is a calcined catalyst, and wherein x is 0.966 and y is 0.033.

2. The catalyst of claim 1, wherein the catalyst is a heterogeneous catalyst.

3. A method of preparing a carbamate, the method comprising:
   contacting a catalyst with at least one amine and at least one alcohol to form a mixture; and
   contacting the mixture with carbon dioxide under conditions sufficient to form the carbamate,
   wherein the catalyst comprises cerium oxide ($CeO_2$) and aluminum (Al) comprising formula $Ce_xAl_yO_2$, wherein the catalyst is a calcined catalyst, and wherein x is 0.966 and y is 0.033.

4. The method of claim 3, wherein the at least one alcohol comprises methanol, ethanol, propanol, butanol, n-hexanol, or a combination of any two or more thereof.

5. The method of claim 3, wherein the at least one amine comprises at least one aliphatic amine.

6. The method of claim 5, wherein the at least one aliphatic amine comprises methylamine, ethylamine, n-propylamine, n-butylamine, n-hexylamine, n-octylamine, or a combination of any two or more thereof.

7. The method of claim 3, wherein the at least one amine comprises at least one aromatic amine.

8. The method of claim 7, wherein the at least one aromatic amine comprises benzylamine.

9. The method of claim 3, wherein a molar ratio of the at least one amine to the at least one alcohol in the mixture is about 1:40 to about 1:200.

10. The method of claim 3, wherein a molar ratio of the at least one amine to the at least one alcohol in the mixture is about 1:100.

11. The method of claim 3, wherein contacting the mixture with the carbon dioxide comprises heating the mixture and the carbon dioxide at a temperature of about 160° C. to about 180° C.

12. The method of claim 3, wherein contacting the mixture with the carbon dioxide comprises heating the mixture and the carbon dioxide at a pressure of about 4.0 MPa to about 7.0 MPa.

13. The method of claim 3, wherein contacting the mixture with the carbon dioxide comprises heating the mixture and the carbon dioxide for about 2 hours to about 16 hours.

14. The catalyst of claim 1, wherein the catalyst further comprises at least one metal selected from the group consisting of iron (Fe), manganese (Mn), titanium (Ti), cobalt (Co), zinc (Zn), calcium (Ca), tin (Sn), indium (In), and a combination of any two or more thereof.

* * * * *